United States Patent [19]
Fanton et al.

[11] Patent Number: 6,068,628
[45] Date of Patent: *May 30, 2000

[54] APPARATUS FOR TREATING CHONDROMALACIA

[75] Inventors: Gary Fanton, Portola; Hugh Sharkey, Redwood City, both of Calif.

[73] Assignee: Oratec Interventions, Inc., Menlo Park, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/700,196

[22] Filed: Aug. 20, 1996

[51] Int. Cl.⁷ .................................................. A61B 17/36
[52] U.S. Cl. ................................ 606/41; 606/28; 606/31; 607/98; 607/99; 607/101
[58] Field of Search ........................... 606/32–34, 39–42, 606/45–52; 607/98, 99, 108, 113, 97, 100, 101; 600/372, 382–384; 604/114

[56] References Cited

U.S. PATENT DOCUMENTS

| | | | |
|---|---|---|---|
| 2,090,923 | 8/1937 | Wappler | 128/303.15 |
| 3,178,728 | 4/1965 | Christensen | 3/1 |
| 3,579,643 | 5/1971 | Morgan | 3/1 |
| 3,776,230 | 12/1973 | Neefe | 128/260 |
| 3,856,015 | 12/1974 | Iglesias | 128/303.15 |
| 3,867,728 | 2/1975 | Substad et al. | 3/1 |
| 3,879,767 | 4/1975 | Substad | 3/1 |
| 3,886,600 | 6/1975 | Kahn et al. | 3/1 |
| 3,938,198 | 2/1976 | Kahn et al. | 3/1.912 |
| 3,945,375 | 3/1976 | Banko | 128/6 |

(List continued on next page.)

FOREIGN PATENT DOCUMENTS

| | | |
|---|---|---|
| 0 257 116 A1 | 3/1988 | European Pat. Off. . |
| 0 274 705 A1 | 7/1988 | European Pat. Off. . |
| 0 479 482 A1 | 4/1992 | European Pat. Off. . |
| 0 521 595 A2 | 1/1993 | European Pat. Off. . |
| 0 542 412 A1 | 5/1993 | European Pat. Off. . |
| 0 558 297 A2 | 9/1993 | European Pat. Off. . |
| 0 566 450 A1 | 10/1993 | European Pat. Off. . |
| 0 572 131 A1 | 12/1993 | European Pat. Off. . |
| 0 682 910 A1 | 11/1995 | European Pat. Off. . |
| 0 479 482 B1 | 5/1996 | European Pat. Off. . |
| 0 729 730 A1 | 9/1996 | European Pat. Off. . |
| 0 737 487 A2 | 10/1996 | European Pat. Off. . |
| 0 783 903 A1 | 7/1997 | European Pat. Off. . |
| 1122634 | 9/1956 | France . |
| 2 645 008 | 3/1989 | France . |

(List continued on next page.)

OTHER PUBLICATIONS

Trimedyne, The Less Invasive Laser Advantage, Omni Spinal Introduction System.

PRNewswire (Dec. 12, 1994), Two Physicians Perform First Outpatient Cervical Disc Procedure Using Laser Technology.

Introduction to the LDD Disc Kit, Oct. 16, 1996.

Mayer et al., Lasers in Percutaneous Disc Surgery: Beneficial Technology or Gimmick?, vol. 25 No. 251 (1993) pp. 38–44.

Schatz et al., Preliminary Experience With Percutaneous Laser Disc Decompression in the Treatment of Sciatica, vol. 38, No. 5, Oct. 1995, pp. 432–436.

(List continued on next page.)

Primary Examiner—Linda C. M. Dvorak
Assistant Examiner—Bryan K. Yarnell
Attorney, Agent, or Firm—Wilson Sonsini Goodrich & Rosati

[57] ABSTRACT

A thermal energy delivery apparatus has a probe including a distal end and a proximal end. A first electrode is positioned at the distal end of the probe such that the electrode is positioned on a recessed longitudinal portion of the probe. The first electrode is configured to deliver sufficient thermal energy to a fibrillated cartilage surface to reduce a level of fibrillation of the fibrillated cartilage surface. A cabling is coupled to the proximal end of the probe.

12 Claims, 7 Drawing Sheets

U.S. PATENT DOCUMENTS

| | | | |
|---|---|---|---|
| 3,987,499 | 10/1976 | Scharbach et al. | 3/1.91 |
| 3,992,725 | 11/1976 | Homsy | 3/1 |
| 4,043,342 | 8/1977 | Morrison, Jr. | 128/303.14 |
| 4,074,718 | 2/1978 | Morrison | 128/303.14 |
| 4,085,466 | 4/1978 | Goodfellow et al. | 3/1.91 |
| 4,129,470 | 12/1978 | Homsy | 156/155 |
| 4,134,406 | 1/1979 | Iglesias | 128/303.15 |
| 4,224,696 | 9/1980 | Murray et al. | 3/1.911 |
| 4,224,697 | 9/1980 | Murray et al. | 3/1.911 |
| 4,326,529 | 4/1982 | Doss et al. | 128/303.1 |
| 4,344,193 | 8/1982 | Kenny | 3/1.911 |
| 4,362,160 | 12/1982 | Hiltebrandt | 128/303.15 |
| 4,375,220 | 3/1983 | Matvias | 128/804 |
| 4,381,007 | 4/1983 | Doss | 128/303.1 |
| 4,397,314 | 8/1983 | Vaguine | 128/399 |
| 4,476,862 | 10/1984 | Pao | 128/303.17 |
| 4,483,338 | 11/1984 | Bloom et al. | 128/303.13 |
| 4,517,965 | 5/1985 | Ellison | 128/20 |
| 4,517,975 | 5/1985 | Garito et al. | 128/303.13 |
| 4,590,934 | 5/1986 | Malis et al. | 128/303.14 |
| 4,593,691 | 6/1986 | Lindstrom et al. | 128/303.14 |
| 4,597,379 | 7/1986 | Kihn et al. | 128/1 R |
| 4,601,705 | 7/1986 | McCoy | 604/94 |
| 4,651,734 | 3/1987 | Doss et al. | 128/303.14 |
| 4,811,733 | 3/1989 | Borsanyi et al. | 128/303.14 |
| 4,815,462 | 3/1989 | Clark | 128/305 |
| 4,838,859 | 6/1989 | Strassmann | 604/95 |
| 4,873,976 | 10/1989 | Schreiber | 128/334 R |
| 4,894,063 | 1/1990 | Nashef | 623/13 |
| 4,895,148 | 1/1990 | Bays et al. | 606/213 |
| 4,907,585 | 3/1990 | Schachar | 606/28 |
| 4,907,589 | 3/1990 | Cosman | 606/34 |
| 4,924,865 | 5/1990 | Bays et al. | 606/77 |
| 4,944,727 | 7/1990 | McCoy | 604/95 |
| 4,950,234 | 8/1990 | Fujioka et al. | 604/60 |
| 4,955,882 | 9/1990 | Hakky | 606/14 |
| 4,966,597 | 10/1990 | Cosman | 606/50 |
| 4,976,709 | 12/1990 | Sand | 606/5 |
| 4,976,715 | 12/1990 | Bays et al. | 606/77 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,085,657 | 2/1992 | Ben-Simhon | 606/42 |
| 5,085,659 | 2/1992 | Rydell | 606/47 |
| 5,098,430 | 3/1992 | Fleenor | 606/42 |
| 5,100,402 | 3/1992 | Fan | 606/41 |
| 5,103,804 | 4/1992 | Abele et al. | 128/4 |
| 5,178,620 | 1/1993 | Eggers et al. | 606/41 |
| 5,186,181 | 2/1993 | Franconi et al. | 128/804 |
| 5,191,883 | 3/1993 | Lennox et al. | 128/401 |
| 5,192,267 | 3/1993 | Shapira et al. | 604/22 |
| 5,201,729 | 4/1993 | Hertzmann et al. | 606/2 |
| 5,201,730 | 4/1993 | Easley et al. | 606/4 |
| 5,201,731 | 4/1993 | Hakky | 606/15 |
| 5,213,097 | 5/1993 | Zeindler | 128/401 |
| 5,230,334 | 7/1993 | Klopotek | 128/399 |
| 5,242,439 | 9/1993 | Larsen et al. | 606/15 |
| 5,242,441 | 9/1993 | Avitall | 606/41 |
| 5,261,906 | 11/1993 | Pennino et al. | 606/46 |
| 5,267,994 | 12/1993 | Gentelia et al. | 606/15 |
| 5,275,151 | 1/1994 | Shockey et al. | 128/4 |
| 5,284,479 | 2/1994 | de Jong | 604/60 |
| 5,304,169 | 4/1994 | Sand | 606/5 |
| 5,308,311 | 5/1994 | Eggers et al. | 606/28 |
| 5,311,858 | 5/1994 | Adair | 128/4 |
| 5,320,115 | 6/1994 | Kenna | 128/898 |
| 5,323,778 | 6/1994 | Kandarpa et al. | 128/653.2 |
| 5,334,193 | 8/1994 | Nardella | 606/41 |
| 5,342,357 | 8/1994 | Nardella | 606/40 |
| 5,348,554 | 9/1994 | Imran et al. | 606/41 |
| 5,352,868 | 10/1994 | Denen et al. | 219/501 |
| 5,354,331 | 10/1994 | Schachar | 623/4 |
| 5,364,395 | 11/1994 | West, Jr. | 606/46 |
| 5,366,443 | 11/1994 | Eggers et al. | 604/114 |
| 5,366,490 | 11/1994 | Edwards et al. | 607/99 |
| 5,382,247 | 1/1995 | Cimino et al. | 606/45 |
| 5,397,304 | 3/1995 | Truckai | 604/95 |
| 5,401,272 | 3/1995 | Perkins | 606/15 |
| 5,415,633 | 5/1995 | Lazarus et al. | 604/95 |
| 5,423,806 | 6/1995 | Dale et al. | 606/15 |
| 5,433,739 | 7/1995 | Sluijter et al. | 607/99 |
| 5,437,661 | 8/1995 | Rieser | 606/15 |
| 5,437,662 | 8/1995 | Nardella | 606/40 |
| 5,451,223 | 9/1995 | Ben-Simhon | 606/42 |
| 5,458,596 | 10/1995 | Lax et al. | 606/31 |
| 5,464,023 | 11/1995 | Viera | 128/772 |
| 5,465,737 | 11/1995 | Schachar | 128/898 |
| 5,484,403 | 1/1996 | Yoakum et al. | 604/59 |
| 5,484,432 | 1/1996 | Sand | 606/5 |
| 5,484,435 | 1/1996 | Fleenor et al. | 606/48 |
| 5,487,757 | 1/1996 | Truckai et al. | 607/122 |
| 5,498,258 | 3/1996 | Hakky et al. | 606/15 |
| 5,500,012 | 3/1996 | Brucker et al. | 607/122 |
| 5,507,812 | 4/1996 | Moore | 623/13 |
| 5,514,130 | 5/1996 | Baker | 606/50 |
| 5,524,338 | 6/1996 | Martyniuk et al. | 29/825 |
| 5,527,331 | 6/1996 | Kresch et al. | 606/170 |
| 5,542,920 | 8/1996 | Cheikh | 604/57 |
| 5,569,242 | 10/1996 | Lax et al. | 606/42 |
| 5,599,346 | 2/1997 | Edwards et al. | 606/41 |
| 5,630,839 | 5/1997 | Corbett, III et al. | 607/137 |
| 5,681,282 | 10/1997 | Eggers et al. | 604/114 |
| 5,683,366 | 11/1997 | Eggers et al. | 604/114 |
| 5,688,270 | 11/1997 | Yates et al. | 606/51 |
| 5,697,909 | 12/1997 | Eggers et al. | 604/114 |
| 5,718,702 | 2/1998 | Edwards | 606/41 |
| 5,782,795 | 7/1998 | Bays | 606/22 |
| 5,810,809 | 8/1998 | Rydell | 606/49 |

FOREIGN PATENT DOCUMENTS

| | | | |
|---|---|---|---|
| 3511107A1 | 10/1986 | Germany. | |
| 3632197A1 | 3/1988 | Germany. | |
| 5-42166 | 5/1993 | Japan. | |
| 637118 | 12/1978 | U.S.S.R. | |
| 1 340 451 | 12/1973 | United Kingdom. | |
| 2 164 473 | 3/1986 | United Kingdom. | |
| WO 85/02762 | 7/1985 | WIPO. | |
| WO 92/10142 | 6/1992 | WIPO | A61B 17/36 |
| WO 93/01774 | 2/1993 | WIPO. | |
| WO 93/16648 | 9/1993 | WIPO. | |
| WO 93/20984 | 10/1993 | WIPO | B26D 1/11 |
| WO 95/01814 | 1/1995 | WIPO | A61N 5/02 |
| WO 95/13113 | 5/1995 | WIPO | A61N 5/02 |
| WO 95/18575 | 7/1995 | WIPO | A61B 17/39 |
| WO 95/20360 | 8/1995 | WIPO. | |
| WO 95/25471 | 9/1995 | WIPO. | |
| WO 95 30377 | 11/1995 | WIPO. | |
| WO 95/30373 | 11/1995 | WIPO. | |
| WO 95/34259 | 12/1995 | WIPO. | |
| WO 96/11638 | 4/1996 | WIPO. | |
| WO 96/32051 | 10/1996 | WIPO. | |
| WO 96/34568 | 11/1996 | WIPO. | |
| WO 96/34571 | 11/1996 | WIPO. | |
| WO 96/39914 | 12/1996 | WIPO | A61B 1/00 |
| WO 97/06855 | 2/1997 | WIPO. | |
| WO 98/07468 | 2/1998 | WIPO. | |

OTHER PUBLICATIONS

Savitz M.A., Same–day Microsurgical Arthroscopic lateri-al–approach Laser–assisted (SMALL) Fluoroscopic Discectomy, vol. 80, Jun. 1994 pp. 1039–1045.

Bosacco et al., Functional Results of Percutaneous Laser Discectomy, Dec. 1996, pp. 825–828.

Sluijter M.E., The Use of Radiofrequency lesions For Pain Relief in Failed Back Patients, vol. 10 No. 1 (1988).

Cosman et al., Theoretical Aspects of Radiofrequency lesions in the Dorsal Root Entry Zone, vol. 15 No. 6 (1984) pp. 945–950.

Wilkins et al., Neurosurgery: Method of Making Nervous System Lesions, ch. 337, pp. 2490–2499.

Yonezawa et al., The System and Procedure of percutaneous Intradiscal Laser Nucleotomy, vol. 15 No. 5 (1990) pp. 1175–1185.

Kolarik et al., Photonucleolysis of Intervertebral Disc and it's Herniation, vol. 51; (1990) pp. 69–71.

Gottlob et al., Lasers in Surgery and Medicine: Holmium:YAG Laser Ablation of Human Intervertebral Disc: Preliminary Evaulation, vol. 12, (1991) pp. 86–91.

Buchelt et al., Lasers in Surgery and Medicine: Fluorescence Guided Excimer Laser Ablation of Intervertebral Discs In Vitro, vol. 11, (1991) pp. 280–286.

Choy et al., Percutaneous Laser Disc Decompression: A New Therapeutic Modality, vol. 17 No. 8, (1992) pp. 949–956.

Sluijter et al., Presistant Pain, Modern Methods of Treatment: Treatment of Chronic Back and neck Pain, vol. 3, (1981) pp. 141–179.

Sluijter, Int Disabil Studies: The use of Radio Frequency Lesions For Pain Relief in Failed Back, vol. 10, Sep. 4, 1996, pp. 37–43.

Shatz et al., CJS JCC Preliminary Experience With Percutaneous Laser Disc Decompression in the Treatment of Sciatica, vol. 38 No. 5, Oct. 1995 pp. 432–436.

Gerber et al., Der Orthopade: Offene Laserchirurgie am Bewegungsapparat, vol. 25, (1996) pp. 56–63.

Gehring W.J., Exploring the Homeobox, (1993), pp. 215–221.

Kelly L.E., Purification and Properties of a 23kDa Ca2+ –binding Protein, (1990) 271, pp. 661–666.

Sluyter, Radiofrequency Lesions in the Treatment of Cervical Pain Syndromes, Radionics, Inc. (1989).

Buchelt et al., Lasers in Surgery and Medicine:Erb:YAG and Hol:YAG Laser Ablation of Meniscus and Intervertebral Discs, vol. 12 No. 4, (1992) pp. 375–381.

Leu et al., Der Orthopade: Endoskopie der Wirbelsaule: Minimal–invasive Therapie, vol. 21, (1992) pp. 267–272.

Phillips et al., JMRI: MR Imaging of Ho; YAG Laser Diskectomy with Histologic Correlation, vol. 3 No. 3, May/Jun. 1993.

Bromm et al., Human Neurobiology: Nerve Fibre Discharges, Cerebral Potentials and Sensations Induced by CO2 laser Stimulation, vol. 3, (1984) pp. 33–40.

Vorwerck et al., Laserablation des Nucleus Pulposus: Optische Eigenschaften von Degeneriertem Bandscheibengewebe im Wellenlangenbereich von 200 bis 2200nm, vol. 151 No. 6, (1989) pp. 725–728.

Wolgin et al., Excimer Ablation of Human Intervertebral Disc at 308 Nanometers, vol. 9, (1989) pp. 124–131.

Davis, Early experience with Laser Disc Decompression, vol. 79 No. 1, (1992)j. Florida M.A.

Quigley et al., Laser Discectomy: Comparison of Systems, vol. 19 No. 3 (1994) pp. 319–322.

Mehta et al., The Treatment of Chronic back Pain: A Preliminary survey of the Effect of Radiofrequency Denervation of the Posterior Vertebral Joints, vol. 34 (1979) pp. 768–775.

Patil et al., Percutaneous Discectomy Using the Electromagnetc Field Focusing Probe: A Feasability Study.

McCulloch et al., CMA Journal: Percutaneous Radiofrequency Lumbar Rhizolysis (rhizotomy), vol. 116, Jan. 8, 1977.

Yonezawa et al., The System and Procedure of Percutaneous Intradiscal Laser Nucleotomy, vol. 15 No. 11 (1990).

Sminia et al., Effects of 434 MHz Microwave Hyperthermia applied to the rat in the region of the cervical Spinal Cord, vol. 3 No. 5 (1987) pp. 441–452.

Sluijter et al., Treatment of Chronic Back and Neck Pain by Percutaneous Therman Lesions, vol. 3 (1981.

Auhll, Richard A., "The Use of the Resectoscope in Gynecology," Biomedical Business International. Oct. 11, 1990, pp. 91–93.

Christian, C. et al., "Allograft Anterior Cruciate Ligament Reconstruction with Patellar Tendon: An Endoscopic Technique", *Operative Techniques in Sports Medicine,* vol. 1, No. 1, Jan. 1993, pp. 50–57.

Houpt, J. et al., "Experimental Study of Temperature Distributions and Thermal Transport During Radiofrequency Current Therapy of the Intervertebral Disc", *Spine,* vol. 21, No. 15, (1996), pp. 1808–1813.

Troussier, B. et al., "Percutaneous Intradiscal Radio–Frequency Thermocoagulation: A Cadaveric Study", *Spine,* vol. 20, No. 15, (Aug. 1995), pp. 1713–1718.

Beadling, L., "Bi–Polar electrosurgical devices: Sculpting the future of arthroscopy", *Orthopedics today,* vol. 17, No. 1, Jan. 1997, 4 pages.

Ellman International Mfg., Inc., 1989, Catalog, pp. 1–15, 20.

Cosset, J.M., Resistive Radiofrequency (Low Frequency) Interstitial Heating (RF Technique), Interstitial Hyperthermia, Dec. 6, 1993, pp. 3–5, 37.

Attachment I: Competitive Literature on Generators with Bipolar Capabilities, IME Co., Ltd., pp. 60–86.

Attachment II: Competitive Literature on Bipolar Forceps and Footswitch Controls, IME Co., Ltd. pp. 87–104.

APPARATUS FOR TREATING CHONDROMALACIA

BACKGROUND OF THE INVENTION

1. Field of the Invention

This invention relates generally to an apparatus for treating chondromalacia, and more particularly to an apparatus that treats chondromalacia with minimal disruption of the cartilage bed of the knee.

2. Description of Related Art

The normal function of joints in humans depends on the distribution of relatively large forces across the body surfaces. In diarthrodial joints the magnitude of the joint forces reaches levels four to seven times body weight. These forces applied to joints are dispersed by articular cartilage. Cartilage function occurs via a highly organized extracellular matrix maintaining a fixed charge density and possessing a high affinity for water.

Normal articular cartilage consists of an assembly of large and small proteoglycans, collagens, hyaluronic acid and glycoproteins. These matrix macromolecules originate from chondrocytes localized in a nonrandom pattern through the cartilage matrix. In normal joints, chondrocytes do not proliferate; dividing chondrocytes indicate a change in cartilage homeostasis, either as regeneration or attempted repair.

Chondromalacia occurs when cartilage beds in joints become worn and strands of cartilage distended away from their respective cartilage beds and extend into the joint capsule. The cartilage surface becomes visibly disrupted, fissured and fibrillated. This has deterious effects on the mechanical properties of articular cartilage. This distension has been associated with knee pain. Treatment to date has included surgical intervention. In one arthroscopic procedure, a shaver is introduced through an arthroscope and is used to remove the strands of disrupted and fibrillated cartilage. However, this treatment can disrupt and remove part of the normal cartilage bed and does not restore a smooth surface nor the mechanical function.

It would be desirable to provide a method and apparatus treating fibrillated cartilage joint surfaces or irregular cartilage joint surfaces by delivering sufficient thermal energy to reduce a level of fibrillation or irregularity of the fibrillated cartilage joint surface or the irregular cartilage joint surface. It would also be desirable to modify the fibrillated cartilage surface to a smooth surface. It would be further desirable to treat chondromalacia by reducing a level of fibrillation or irregularity of a fibrillated or irregular cartilage joint surface.

SUMMARY OF THE INVENTION

Accordingly, an object of the invention is to provide a method and apparatus for treating fibrillated or irregular cartilage joint surfaces.

Another object of the invention is to provide a method and apparatus for delivering sufficient thermal energy to reduce a level of fibrillation of a fibrillated cartilage joint surface.

Yet another object of the invention is to provide a method and apparatus for delivering sufficient thermal energy to modify a fibrillated cartilage joint surface to a smooth surface.

A further object of the invention is to provide a method and apparatus for delivering sufficient thermal energy to modify an irregular cartilage joint surface to a smoother surface.

Still a further object of the invention is to provide a method and apparatus for delivering sufficient thermal energy to at least a portion of a plurality of cartilage strands coupled to a fibrillated cartilage surface, and melt the strands onto the fibrillated cartilage surface.

Another object of the invention is to provide a method and apparatus that uses thermal energy to treat chondromalacia.

These and other objects of the invention are achieved in a thermal energy delivery apparatus that has a probe means including a distal end and a proximal end. A first electrode means is positioned at the distal end of the probe means. The first electrode means is configured to deliver sufficient thermal energy to a fibrillated cartilage surface to reduce a level of fibrillation of the fibrillated cartilage surface. A cabling means is coupled to the proximal end of the probe means.

In one embodiment of the invention, an apparatus is configured to be positioned adjacent to a fibrillated cartilage joint surface. A probe means has a distal end and a proximal end. An insulator means has a first surface and a second surface. A first electrode means is positioned on the first surface of the insulator. The first electrode means has a first thermal energy delivery surface configured to deliver sufficient thermal energy to a plurality of cartilage strands coupled to the fibrillated cartilage joint surface to reduce a level of fibrillation of surface. A second electrode means is positioned on the second surface of the insulator. A cable means is coupled to the proximal end of the probe means.

In another embodiment, a method modifies a geometry of a fibrillated cartilage surface. A thermal energy delivery device is provided and includes a probe means with a distal end and a thermal energy delivery surface. A thermal energy source is also provided and coupled to the thermal energy delivery surface. The thermal energy delivery surface is positioned adjacent to the fibrillated cartilage surface in a non-contacting position. Sufficient thermal energy is delivered from the thermal energy delivery surface to reduce a level of fibrillation of the fibrillated cartilage surface.

The method and apparatus of the present invention can also be used to decrease the level of irregularity of an irregular cartilage surface.

The apparatus of the present invention may also include a sensor means positioned at the distal end of the probe means. A comparator means is provided and compares a measured temperature value at the sensor means with a predetermined temperature value. The comparator means generates a disabling signal if the measured temperature value exceeds the predetermined maximum temperature value. A communication means is provided and communicates the disabling signal to the thermal energy source means to cease farther delivery of energy from the thermal energy source means to the first electrode means.

In various embodiments of the invention, sufficient thermal energy is delivered from the thermal energy delivery surface to modify the fibrillated cartilage surface to a smooth surface. Thermal energy is delivered from the thermal energy delivery surface to create a less fibrillated, fibrillated cartilage surface. Thermal energy is delivered from the thermal energy delivery surface to cause at least a portion of a plurality of cartilage strands coupled to the fibrillated cartilage surface to create a smoothened cartilage surface. Thermal energy is delivered from the thermal energy delivery surface to cause at least a portion of a plurality of cartilage strands coupled to the fibrillated cartilage surface to melt onto the fibrillated cartilage surface. At least a portion of a plurality of cartilage strands are melted to create a smoothened cartilage surface.

DETAILED DESCRIPTION

Figure 1:
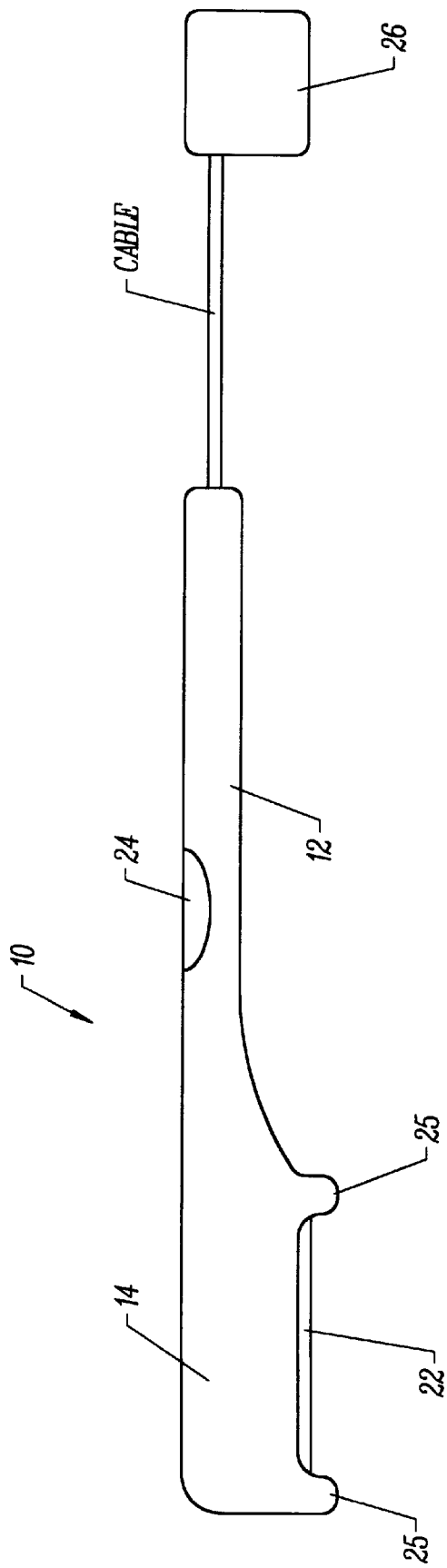
FIG. 1 is a perspective view of the apparatus of the present invention with a probe and two electrodes.

As shown in FIG. 1, a thermal energy delivery apparatus 10 is configured to be positioned adjacent to, but spaced apart from a joint surface. Included is a probe 12 with a distal end 14, a first electrode 22 and a second electrode 24. Electrodes 22 and 24 can be operated in bipolar or monopolar. Bipolar is preferred. A distancing element 25 distances a thermal energy delivery surface of electrode 22 from the joint surface. Preferably, the thermal energy delivery surface of electrode 22, or of electrode 24, does not touch the joint surface. As illustrated in FIG. 1, distancing element 25 is included. In other embodiments, distancing element 25 is not included and the thermal energy delivery surface of electrode 22 or of electrode 24 are positioned directly on the joint surface.

Figure 2:
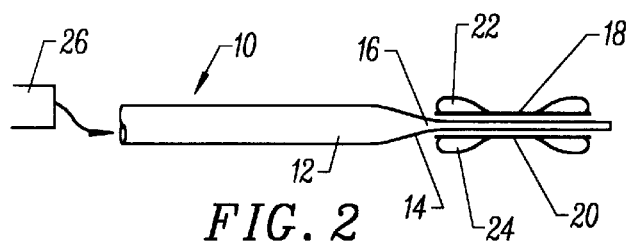
FIG. 2 is a perspective view of the apparatus of the present invention with a probe, an electrode positioned at a distal end of the probe and two electrodes positioned on opposite sides of an insulator.

Referring now to FIG. 2, thermal energy delivery apparatus 10 is configured to be positioned and deliver thermal energy to a joint surface. Apparatus 10 includes probe 12 with distal end 14 and an insulator 16 including first and second surfaces 18 and 20 formed on opposite sides on insulator 16. A pair of electrodes are also provided. First electrode 22 is positioned on first surface 18 of insulator 16. Second electrode 24 is positioned on second surface 20 of insulator 16. Thermal energy source 26 is coupled to first electrode 22 and second electrode 24 with a cable.

Insulator 16 can be an elongated structure with a longitudinal axis. Surfaces 18 and 20 can be parallel to each other. Insulator can be made of a variety of insulating materials known to those skilled in the art. Insulator 16 need not be one integral unit and surfaces 18 and 20 can be made of separate insulators that are separated. Surfaces 18 and 20 can be planar, non-planar and have geometries that conform closely to interior joint surfaces. In one embodiment, the dimensions of distal end 14 are sufficiently small to be positioned on a joint surface.

Figure 3:
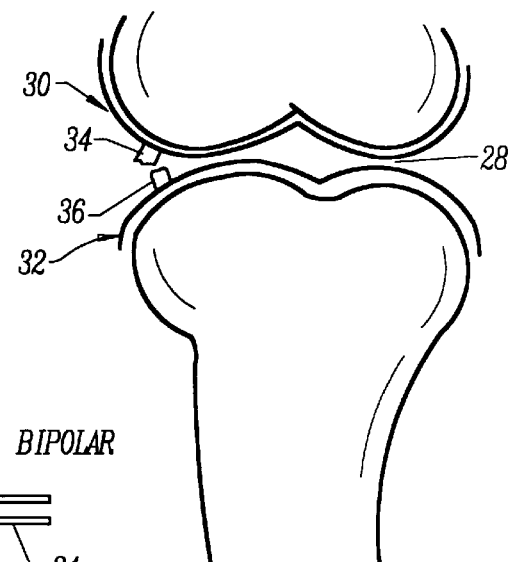
FIG. 3 is a perspective view of a knee joint with chondromalacia.

A knee joint surface 28 is shown in FIG. 3. Knee joint surface 28 is defined by a first cartilage bed 30 formed at a distal end of the femur, and a second cartilage bed 32 formed at a distal end of the tibia. The present invention is not limited to the knee joint surface and can be used in a variety of different joint surfaces. Any joint surface susceptible to chondromalacia is treatable with apparatus 10. The present invention is suitable for the treatment of fibrillated cartilage joint surfaces to reduce the level of fibrillation and create smoother surfaces. The present invention is also used to treat irregular joint surfaces, where there are peaks and valleys, and create a less irregular joint surface. In certain embodiments, the irregular joint surface becomes a smooth joint surface.

A first plurality of cartilage strands 34 are coupled to first cartilage bed 30 and have become dislodged and dangle in joint surface 28. A second plurality of cartilage strands 36 are connected to second cartilage bed 32. Second plurality of cartilage strands 36 have also become dislodged and dangle in joint surface 28.

In one embodiment of the invention, a method is provided that modifies a geometry of a fibrillated cartilage surface. Sufficient thermal energy is delivered from first electrode 22 or second electrode 24 at different times to reduce a level of fibrillation of the fibrillated cartilage joint surface. In various embodiments of the invention, sufficient thermal energy is delivered electrode 22 or 24 to, (i) change the fibrillated cartilage surface to a smooth or smoother surface, (ii) reduce a level of fibrillation of the fibrillated cartilage surface, (iii) cause at least a portion of a plurality of cartilage strands coupled to the fibrillated cartilage surface to create a smoothened cartilage surface, (iv) cause at least a portion of a plurality of cartilage strands coupled to the fibrillated cartilage surface to melt onto the fibrillated cartilage surface or (v) melt at least a portion of a plurality of cartilage strands to create a smoothened cartilage surface.

First electrode 22 has a first thermal energy delivery surface configured to deliver thermal energy to cartilage strands 34 and second electrode 24 has a second thermal energy delivery surface configured to deliver thermal energy to cartilage strands 36. Thermal energy includes but is not limited to RF, microwave, resistive heating, ultrasound, coherent or incoherent light and a thermal jet source. By delivering the appropriate amount of thermal energy to joint surface 2286, strands 34 and 36 move out of joint surface 26 and the surfaces of cartilage beds 30 and 32 are smoothened. Additionally, delivered thermal energy can remove some or substantially all of cartilage strands 34 and 36 from joint surface 28. The delivery of thermal energy physically smooths the surface of cartilage beds 30 and 32, changes the ultrastructure of the cartilage, stimulates cartilage replication and growth and changes the chemical environment in joint surface 28 and cartilage beds 30 and 32 to relieve pain.

Apparatus 10 is used to modify the geometry of cartilage strands 34 and 36 through cartilage shrinkage and possibly limited ablation of strands 34 and 36. Distal end 14 of probe 12 is inserted through an arthroscope to joint surface 28. First and second electrodes 22 and 24 are introduced into joint surface 28. Sufficient thermal energy is delivered from electrodes 22 and 24 to shrink at least a portion of cartilage strands 34 and 36, causing the strands to lie down on cartilage beds 30 and 32. The delivery of thermal energy to joint surface 28 results in an "ironing" of cartilage strands 34 and 36 onto cartilage beds 30 and 32.

Sufficient nonfulgarating thermal energy is delivered from first and second electrodes 22 and 24 to shrink at least a portion of cartilage strands 34 and 36 without ablating more than 25% of cartilage beds 30 and 32. In one embodiment, sufficient energy is delivered by first and second electrodes 22 and 24 to raise the temperature of joint surface in the range of 45 to 90 degrees C, preferably 45 to 75 degrees C and more preferably 50 to 70 degrees C. Maintenance of a suitable temperature, and the delivery of thermal energy to joint surface 28, is sufficient to cause strands 34 and 36 to become at least partially melted onto the cartilage joint surface while minimizing ablation of cartilage beds 30 and 32.

Insulator 16 and first and second electrodes 22 and 24 are configured to be inserted into joint surface 28. Probe 12 is moved back and forth through joint surface 28 to deliver a sufficient amount of thermal energy to strands 34 and 36 to cause them to lie down on their respective cartilage beds. The thermal energy delivery surfaces of first and second electrodes 22 and 24 can move along the surfaces of cartilage beds 30 and 32 to complete the ironing effect.

Figure 4:
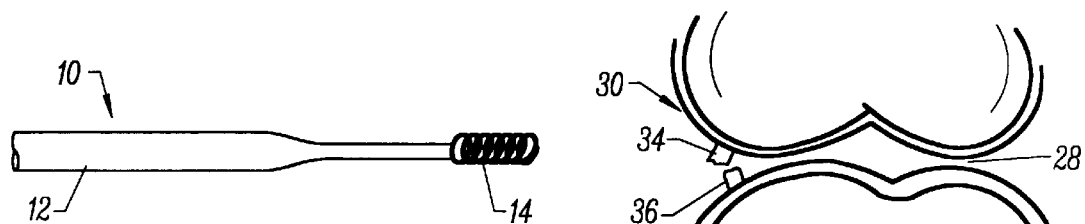
FIG. 4 is a perspective view of the apparatus of FIG. 2 with a probe coiled distal end.

Referring now to FIG. 4, distal end 14 of probe 12 can have a coiled geometry as well as a variety of geometric configurations. Preferably, distal end 14 is malleable or sufficiently flexible to impart movement of first and second electrodes 22 and 24. Distal end 14 can pivot, be hinged, be articulated, or made of a shaped memory metal, and the like, in order to enable first and second electrodes 22 and 24 to follow the contours of joint surface 28.

Figure 5:
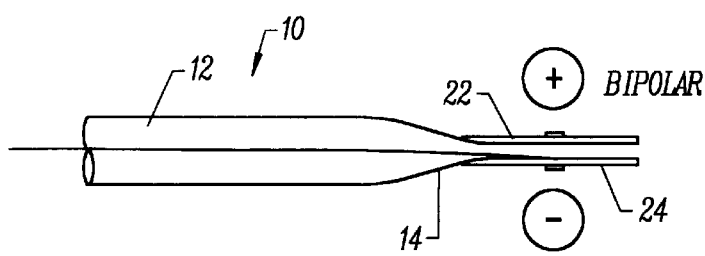
FIG. 5 is a perspective view of the apparatus of the present invention with two electrodes positioned on opposite sides of an insulator.

As shown in FIG. 5, first and second electrodes 22 and 24 can be operated in a bipolar mode. This concentrates the flow of RF energy between first and second electrodes 22 and 24 and diverts direct RF energy flow away from cartilage beds 30 and 32. RF energy which is directed between first and second electrodes 22 and 24 heats up fluids within joint surface 28 and provides a more controlled delivery of energy to cartilage strands 34 and 36. RF ablation of cartilage beds 30 and 32 is reduced.

Figure 6:
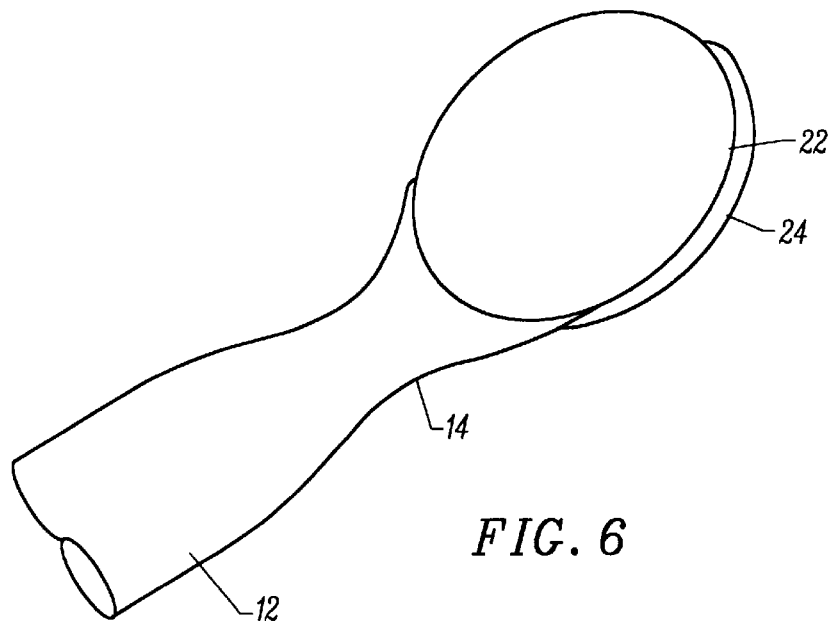
FIG. 6 is perspective view of the apparatus of the present invention including an electrode with radiused edges.
Figure 7:
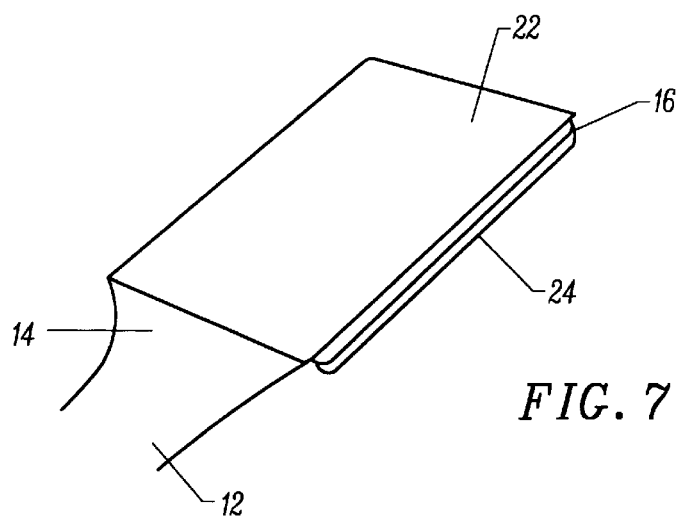
FIG. 7 is a perspective view of the apparatus of the present invention including a rectangularly shaped electrode.

First and second electrodes 22 and 24 can have a variety of different geometric configurations. As illustrated in FIG. 6, first and second electrodes 22 and 24 are symmetrically shaped with radiused edges. Elimination of sharp edges at an electrode surface reduce the creation of hot spots of thermal energy delivered to a site. In FIG. 7, first and second electrodes 22 and 24 have rectangular geometries with non-radiused edges. First and second electrodes 22 and 24 can each have different sizes and geometries. First and second electrodes 22 and 24 can be mirror images of each other or they can be different.

Figure 8:
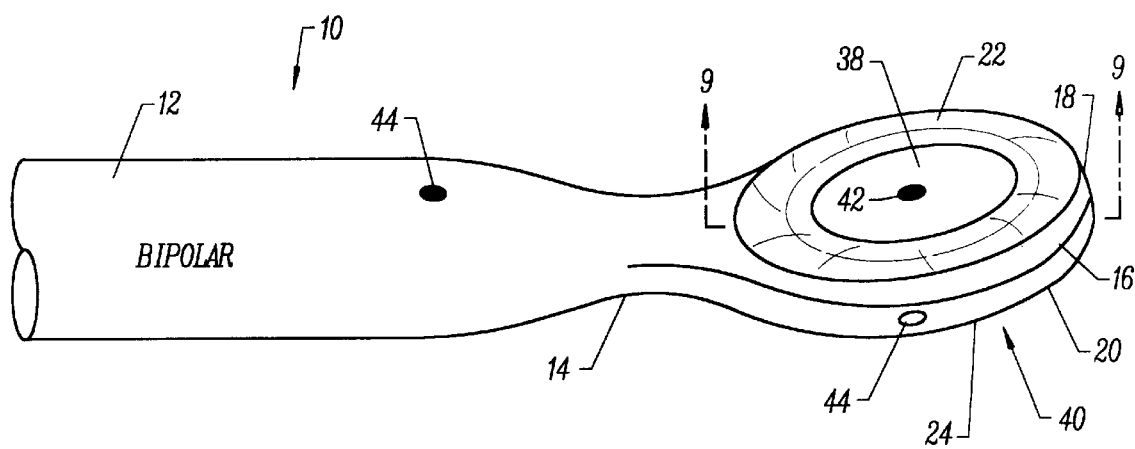
FIG. 8 illustrates a perspective view of the apparatus of the present invention with electrodes formed on peripheral faces of the insulator.

Referring now to FIG. 8, first and second electrodes 22 and 24 are formed on a periphery of insulation surfaces 18 and 20 respectively. In this embodiment, each electrode 22 and 24 defines a first and a second non-conducting region 38 and 40 on an insulator surface 18 and 20 within an interior of first and second electrodes 18 and 20. Non-conducting regions 38 and 40 can be the actual surface of insulator 16, or may be additional structures, each with a non-conducting surface, that are formed on insulation surfaces 18 and 20.

First and second sensors 42 and 44 can be provided and associated with first and second electrodes 22 and 24 to measure temperature and/or impedance. First and second sensors 42 and 44 are positioned on a surface of first and second electrodes 22 and 24, on a surface of probe 12, on non-conducting regions 38 and 40, or can be advanced and retracted from distal end 14 to and from joint surface 28.

First and second sensors 42 and 44 are of conventional design, including but not limited to thermistors, thermocouples, resistive wires, and the like. Suitable thermal sensors 42 and 44 include a T type thermocouple with copper constantene, J type, E type, K type, fiber optics, resistive wires, thermocouple IR detectors, and the like. Sensors 42 and 44 need not be thermal sensors.

Sensors 42 and 44 measure temperature and/or impedance to permit monitoring and a desired level of energy delivered determined This reduces ablation damage to cartilage beds 30 and 32. If at any time sensor 42 or 44 determines that a desired temperature is exceeded, then an appropriate feedback signal is received at thermal energy source 26 which then regulates the amount of energy delivered to first and second electrodes 22 and 24.

Figure 9:
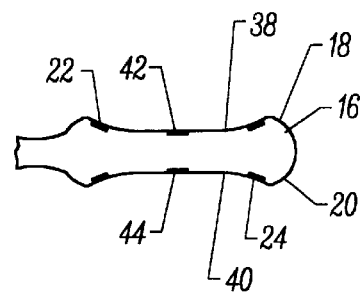
FIG. 9 is a cross-sectional view of the apparatus of FIG. 8 taken along the lines 9—9.

Sensors 42 and 44 are positioned on non-conducting regions 38 and 40 in FIG. 9. Non-conducting regions 38 and 40 have a variety of geometric surfaces including but not limited to planar, non-planar, concave, convex, and the like. In one embodiment, non-conducting regions 38 and 40 are closer to the midline of insulator 16 than first and second electrodes 22 and 24. This enhances the bipolar conduction of thermal energy between electrodes 22 and 24 in the bipolar mode of operation.

Figure 10:
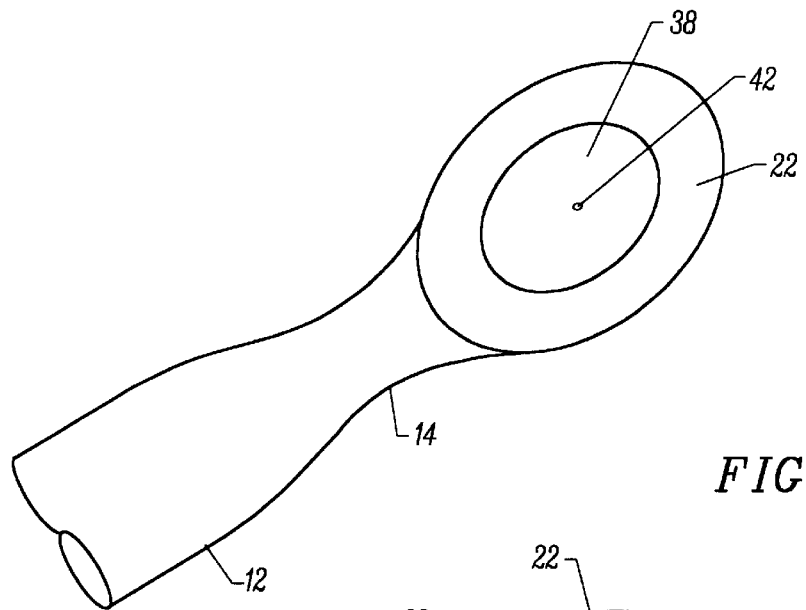
FIG. 10 is a perspective view of an electrode used with the apparatus of the present invention that is formed at a peripheral surface of the insulator and defines an interior non-conducting region.
Figure 11:
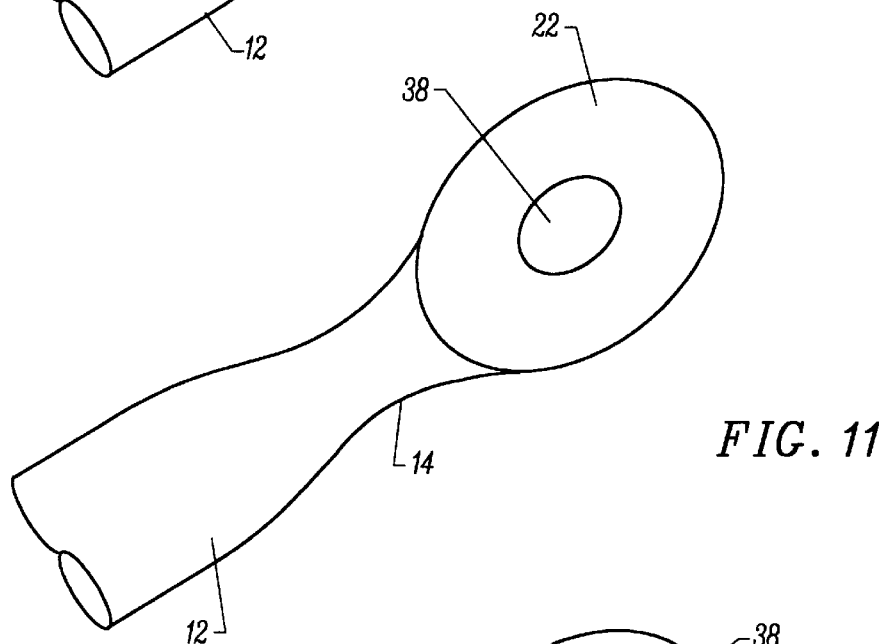
FIG. 11 is a perspective view of a toroidal electrode used with the apparatus of the present invention and defines an interior non-conducting region.
Figure 12:
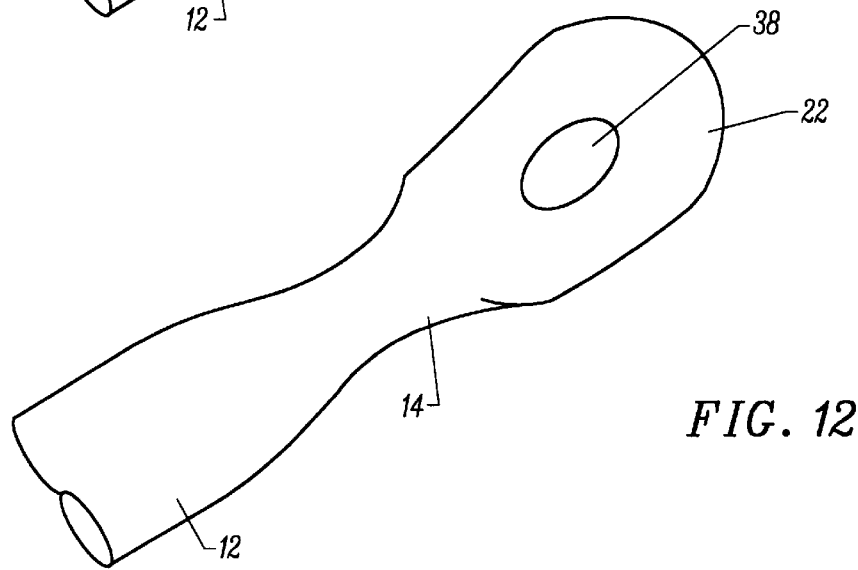
FIG. 12 is a perspective view of a non-circular toroidal electrode used with the apparatus of the present invention and defines an interior non-conducting region.
Figure 13:
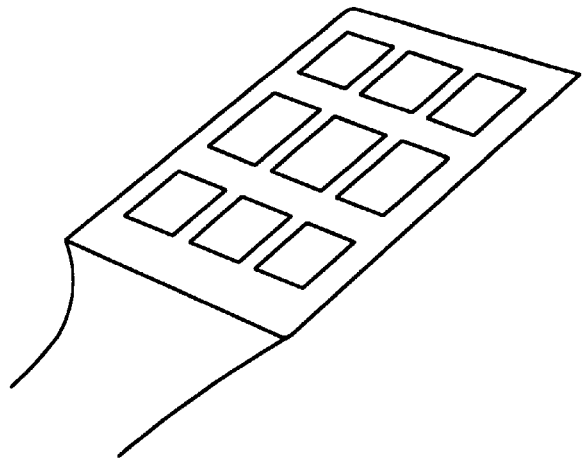
FIG. 13 is a perspective view of a segmented electrode used with the apparatus of the present invention.
Figure 14:
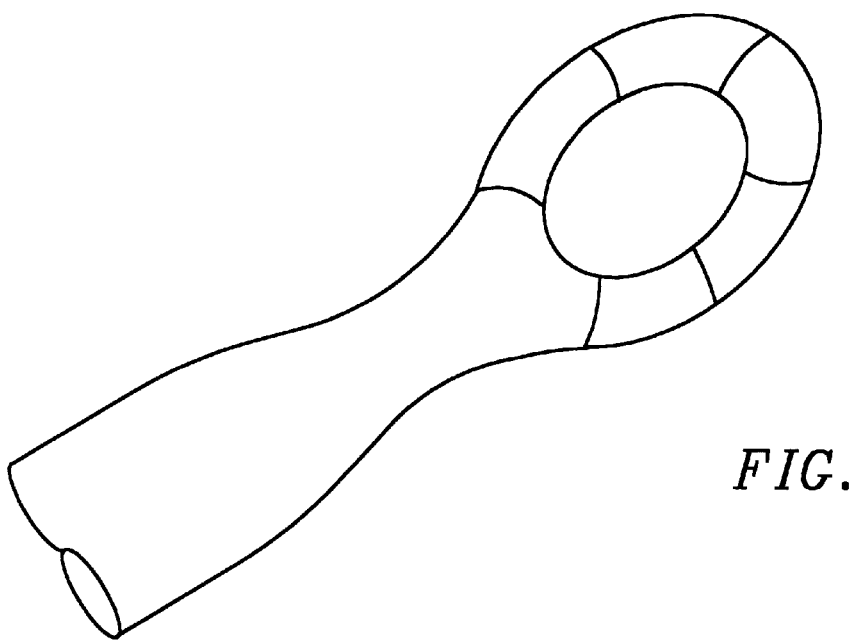
FIG. 14 is a perspective view of a segmented toroidal electrode used with the apparatus of the present invention.
Figure 15:
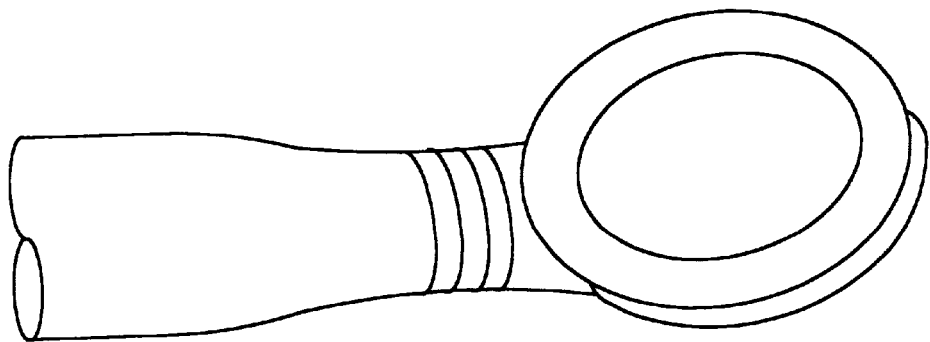
FIG. 15 is a perspective view of a flexible probe used with the apparatus of the present invention.

First and second electrodes 22 and 24 can have various geometries including but not limited to cylindrical, semi-cylindrical, rectangular, cubic, irregularly shaped, toroidal (FIG. 10), non-circular toroidal (FIG. 11), non-symmetrical, non-symmetrical toroidal (FIG. 12) or be segmented and capable of multiplexing (FIGS. 13 and 14). In one embodiment, first electrode 22 has a toroidal geometry, first sensor 42 is positioned on non-conducting region 38, and distal end 14 is flexible and curved.

Figure 16:
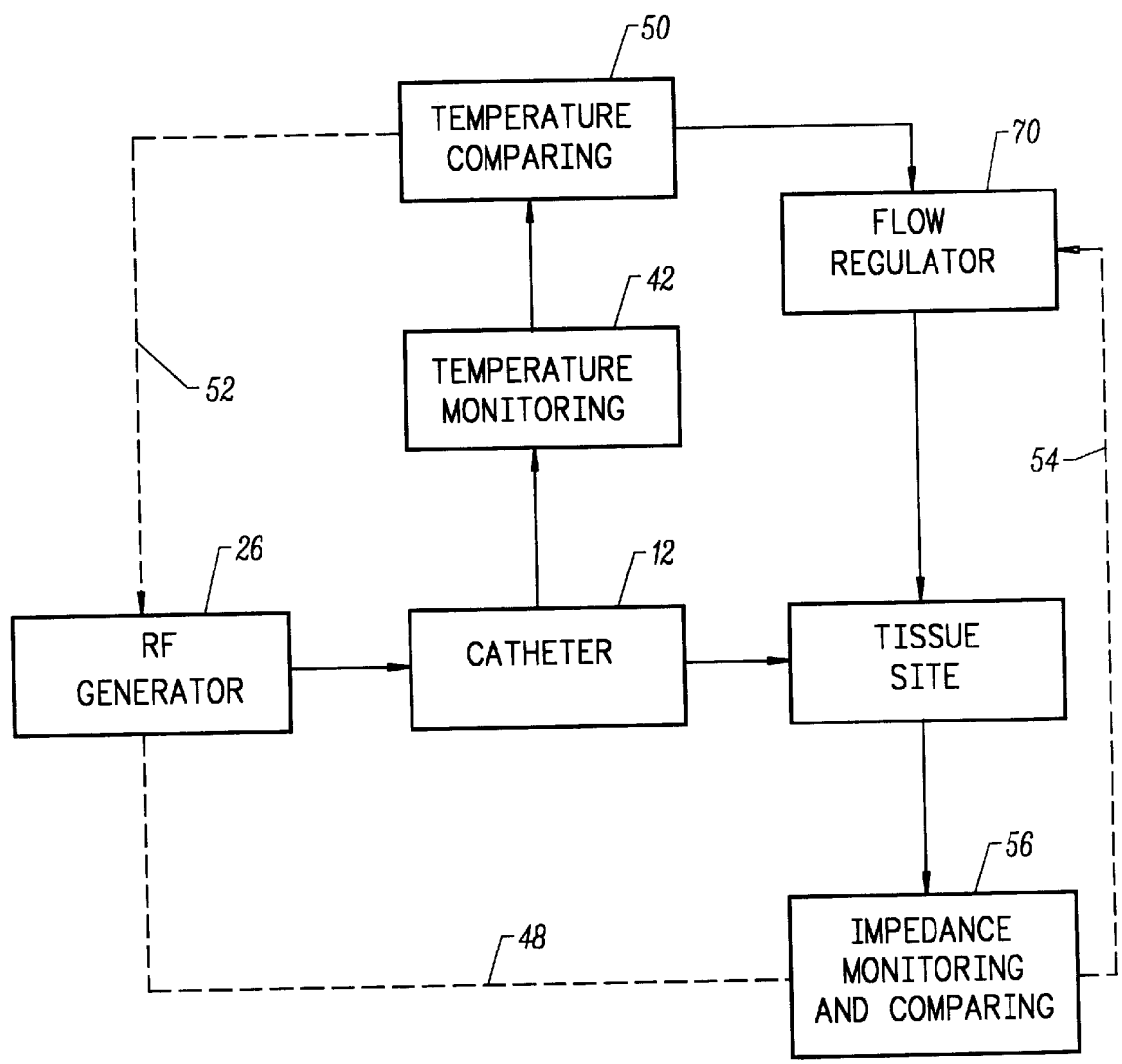
FIG. 16 is a block diagram illustrating a feedback system useful to control the temperature of electrodes of the present invention.

FIG. 16 illustrates a block diagram of a temperature/impedance feedback system useful with apparatus 10. Thermal energy is delivered to first and second electrodes 22 and 24 by thermal energy source 26, and applied to cartilage strands 34 and 36. A monitor 56 ascertains tissue impedance, based on the energy delivered to tissue, and compares the measured impedance value to a set value. If the measured impedance exceeds the set value a disabling signal 48 is transmitted to thermal energy source 26, ceasing further delivery of thermal energy to first and second electrodes 22 and 24. If measured impedance is within acceptable limits, energy continues to be applied. During the application of thermal energy to cartilage strands 34 and 36, sensor 42 measures the temperature at the surface of sensor 42. A comparator 50 receives a signal representative of the measured temperature and compares this value to a pre-set signal representative of the desired temperature. Comparator 50 sends a signal to thermal energy source 26 to continue sending thermal energy, to increase or decrease the level of delivered thermal energy, or to cease delivery of thermal energy.

An output 52 from temperature comparator 50 can be input to thermal energy source 26 to regulate the amount of power delivered. Output 54 from impedance monitor 56 can be input control the temperature at joint surface 28.

Figure 17:
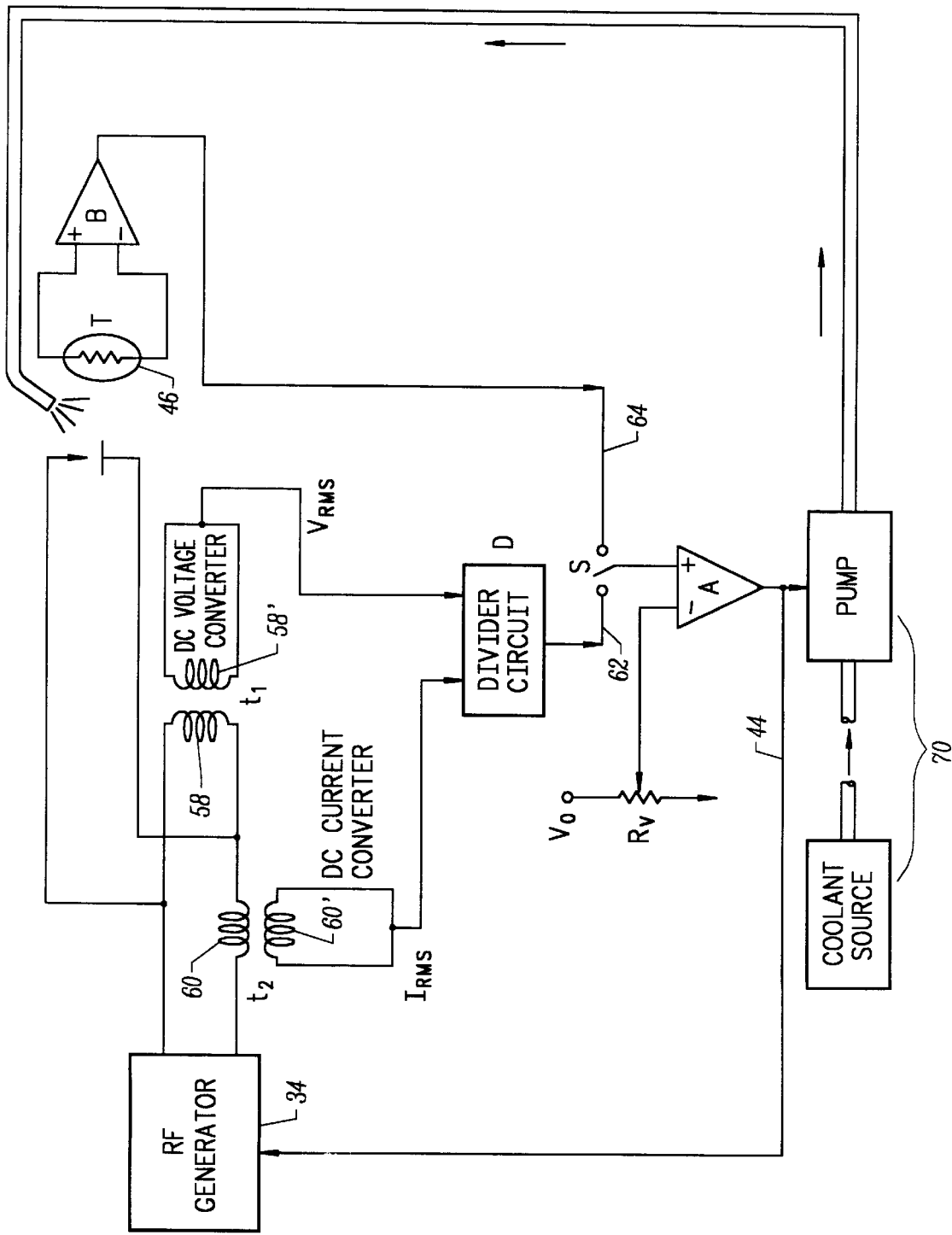
FIG. 17 illustrates a circuit useful to implement the feedback system of FIG. 16.

Referring now to FIG. 17, thermal energy source 26 is coupled to first and second electrodes 22 and 24 and apply a biologically safe voltage to cartilage strands 34 and 36. In the embodiment illustrated in FIG. 11, apparatus 10 is represented as a bipolar ablation device. First and second electrodes 22 and 24 are connected to a primary side of transformer windings 58 and 60. The common primary windings 58 and 60 are magnetically coupled with a transformer core to secondary windings 58' and 60'.

The primary windings 58 of the first transformer $t_1$ couple the output voltage of apparatus 10 to the secondary windings 58'. The primary windings 60 of the second transformer $t_2$ couple the output current of ablation apparatus 10 to the secondary windings 60'.

Measuring circuits determine the root mean square (RMS) values or magnitudes of the current and voltage. These values, represented as voltages, are inputted to a diving circuit D to geometrically calculate, by dividing the RMS voltage value by the RMS current value, the impedance of the tissue site at sensor 42.

The output voltage of the divider circuit D is presented at the positive (+) input terminal of comparator A. A voltage source $V_o$ supplies a voltage across the variable resistor $R_v$, thus allowing one to manually adjust the voltage presented at the negative input of comparator A. This voltage represents a maximum impedance value beyond which power will not be applied to electrode 22. Specifically, once the tissue is heated to a temperature corresponding to an impedance value greater than the maximum cut-off impedance, thermal energy source 26 stops supplying energy to first and second electrodes 22 and 24. Comparator A can be of any of a commercially available type that is able to control the amplitude or pulse width modulation of thermal energy source 26.

The temperature within joint surface 28 can be controlled based on the tissue impedance, as represented by signal 62, or based on tissue temperature, as represented by signal 64. In one embodiment, the switch S is activated to allow the impedance signal 62 to enter the positive (+) input terminal of comparator A. This signal along with the reference voltage applied to the negative (−) input terminal actuates comparator A to produce an output signal. If the selected tissue ablation site is heated to a biologically damaging temperature, the tissue impedance will exceed a selected impedance value seen at the negative (−) input terminal, thereby generating disabling signal 48 to disable thermal energy source 26, ceasing the energy supplied to first and second electrodes 22 and 24.

The output signal of comparator A may either disable thermal energy source's 26 energy output, depending on the tissue temperature as reflected by its impedance.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A thermal energy delivery apparatus comprising:
   a distal portion having longitudinal surfaces extending distally to a distal end, a portion of the longitudinal surfaces including a recessed portion such that the recessed portion is positionable adjacent a fibrillated cartilage joint surface; and
   a electrode positioned within the recessed portion at a first depth which when the recessed portion is positioned adjacent fibrillated cartilage tissue of a joint surface is (a) less than a depth where fibrils extending from the fibrillated cartilage tissue would not be able to contact the electrode, and (b) greater than a depth where the electrode would contact the cartilage tissue underlying the fibrils.

2. The apparatus of claim 1, further comprising a cabling coupled to the proximal end of the apparatus.

3. The apparatus of claim 1, further comprising a second electrode positioned on the apparatus such that the first electrode delivers energy through the fibrils adjacent the first electrode to the second electrode.

4. The apparatus of claim 3, wherein the first electrode and the second electrode are positioned on opposite sides of the apparatus to minimize damage to the cartilage tissue underlying the fibrils.

5. The apparatus of claim 1, wherein the apparatus is a bipolar device.

6. The apparatus of claim 1, wherein the apparatus is a monopolar device.

7. The apparatus of claim 1, further comprising a sensor positioned at the distal end of the probe.

8. The apparatus of claim 1, further comprising a thermal energy source coupled to the first electrode.

9. The apparatus of claim 8, further comprising:
   a sensor positioned at the distal end of the apparatus;
   a comparator configured for comparing a measured temperature value at the sensor with a predetermined temperature value and generating a disabling signal if the measured temperature value exceeds the predetermined maximum temperature value; and
   a communication means for communicating the disabling signal to the thermal energy source to cease further delivery of energy from the thermal energy source to the first electrode.

10. The apparatus of claim 1, wherein the thermal energy source is selected from the group consisting of RF, microwave, resistive heating, ultrasound, coherent light, incoherent light and liquid thermal jet.

11. The apparatus of claim 1, wherein the distal end of the apparatus is sized to contract a joint.

12. The apparatus of claim 11, wherein the distal end of the apparatus is sized to contract an articulated joint.

* * * * *